(12) United States Patent
Suzuki

(10) Patent No.: US 9,074,991 B2
(45) Date of Patent: Jul. 7, 2015

(54) MEASURING APPARATUS

(75) Inventor: Koichi Suzuki, Kodaira (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 353 days.

(21) Appl. No.: 13/583,129

(22) PCT Filed: Apr. 22, 2011

(86) PCT No.: PCT/JP2011/002386
§ 371 (c)(1),
(2), (4) Date: Sep. 6, 2012

(87) PCT Pub. No.: WO2011/135821
PCT Pub. Date: Nov. 3, 2011

(65) Prior Publication Data
US 2012/0325006 A1    Dec. 27, 2012

(30) Foreign Application Priority Data
Apr. 27, 2010    (JP) ................... 2010-102312

(51) Int. Cl.
| | |
|---|---|
| *A61B 8/00* | (2006.01) |
| *G01N 21/00* | (2006.01) |
| *G01N 29/00* | (2006.01) |
| *G01N 21/17* | (2006.01) |
| *A61B 5/00* | (2006.01) |

(Continued)

(52) U.S. Cl.
CPC .......... *G01N 21/1702* (2013.01); *A61B 5/0095* (2013.01); *A61B 5/4312* (2013.01); *A61B 8/485* (2013.01); *G01N 21/4795* (2013.01); *G01N 21/49* (2013.01); *G01N 2021/1787* (2013.01); *G01N 2201/0697* (2013.01)

(58) Field of Classification Search
CPC .... A61B 5/0095; A61B 5/4312; A61B 8/485; G01N 21/1702; G01N 21/4795; G01N 2021/1787; G01N 21/49; G01N 2201/0697
USPC .................................................... 73/655, 643
See application file for complete search history.

(56) References Cited

U.S. PATENT DOCUMENTS

| | | | | |
|---|---|---|---|---|
| 4,603,973 | A | * | 8/1986 | Crow ........................... 356/5.04 |
| 5,772,588 | A | * | 6/1998 | Miwa et al. ................... 600/310 |

(Continued)

FOREIGN PATENT DOCUMENTS

| | | |
|---|---|---|
| JP | 2000-343256 | 12/2000 |
| JP | 2010-017426 | 1/2010 |

(Continued)

*Primary Examiner* — J M Saint Surin
(74) *Attorney, Agent, or Firm* — Fitzpatrick, Cella, Harper & Scinto

(57) ABSTRACT

A measuring apparatus includes: laser sources; and a control unit for outputting an excitation start signal that instructs the laser light sources to start excitation, and outputting an oscillation start signal to instruct the laser light sources to start oscillation after a predetermined time has elapsed from the output of the excitation start signal, so as to generate pulsed light from the laser light sources. The laser sources include a first laser source and a second laser source of which preparation time from the start of the excitation to the generation of the pulsed light is longer than that of the first laser source. The control unit sets timing to output the excitation start signal to the first laser source to follow timing to output the excitation start signal to the second laser source according to a difference of the preparation time between the first and second laser sources.

10 Claims, 12 Drawing Sheets

(51) Int. Cl.
*G01N 21/47* (2006.01)
*A61B 8/08* (2006.01)
*G01N 21/49* (2006.01)

(56) References Cited

U.S. PATENT DOCUMENTS

| | | | |
|---|---|---|---|
| 5,948,935 A * | 9/1999 | Ferland et al. | 560/122 |
| 7,329,884 B2 * | 2/2008 | Kondo et al. | 250/492.22 |
| 7,710,566 B2 * | 5/2010 | Arnott et al. | 356/432 |
| 8,342,028 B2 * | 1/2013 | Ichihara et al. | 73/643 |
| 2007/0299341 A1 | 12/2007 | Wang et al. | 600/443 |
| 2011/0112391 A1 | 5/2011 | Nishihara et al. | 600/407 |
| 2011/0231160 A1 | 9/2011 | Suzuki | 702/189 |
| 2012/0209104 A1 | 8/2012 | Suzuki | 600/407 |

FOREIGN PATENT DOCUMENTS

| | | |
|---|---|---|
| WO | WO 2010/005109 | 1/2010 |
| WO | WO 2010/005116 | 1/2010 |

* cited by examiner

MEASURING APPARATUS

TECHNICAL FIELD

The present invention relates to a measuring apparatus for measuring spectral characteristics inside a biological tissue using a photoacoustic effect.

BACKGROUND ART

Many measuring apparatuses, in which a pulsed light is irradiated onto a biological object, a photoacoustic wave generated from inside the biological object is received by a probe, and the forms and functions inside the biological tissue are displayed as images, have been proposed in medical fields. This technology is called "photoacoustic tomography (PAT) ". In such an apparatus, the intensity of the light irradiated into the biological tissue attenuates while propagating inside the biological tissue due to absorption and scattering, hence only very little light reaches the depth of the tissue. As a result, photoacoustic waves are generated inside the biological tissue, and electric signals (photoacoustic signals) converted by the probe become weak. To prevent this, a Q switch is installed in the light source to perform rapid oscillation, so that the quantity of pulsed light is increased, and a higher quantity of light reaches the depth.

An apparatus, in which a plurality of light sources are installed so as to increase the quantity of light that reaches the depth of a subject by simultaneously irradiating pulsed light onto the subject from both sides thereof, has also been proposed in Japanese Patent Application Laid-Open No. 2010-017426.

An example of the conventional measuring apparatus will be described with reference to FIG. 12A. FIG. 12A shows a configuration of the conventional measuring apparatus. The reference numeral 81 is a biological tissue, that is a subject, 82a and 82b are pulsed lights, and 87 is a light absorbing area existing inside the subject. The light absorbing area refers to an area which absorbs energy of the pulsed light, and generates a photoacoustic wave efficiently, and an example is a blood vessel. 88 is a photoacoustic wave generated from the light absorbing area 87, 85 is a probe for converting the photoacoustic wave 88 into an electric signal, and 86a and 86b are plate members for securing the subject 81. A direction from the probe 85 to the subject 81 is a Z direction, a vertical direction from top to bottom is a Y direction, and an X direction is a horizontal direction which is orthogonal to the Z direction and the Y direction. If the pulsed lights 82a and 82b are irradiated onto the subject 81, the photoacoustic wave 88 is generated from the light absorbing area 87. This wave is converted into an electric signal (photoacoustic signal) by the probe 85, and is then converted into a diagnostic image by an electric circuit, which is not illustrated, and is output. The timings of irradiating the pulsed lights 82a and 82b and the timings of receiving the photoacoustic signals are controlled by a controller, which is not illustrated.

A laser processing apparatus which can control the emission timings of a plurality of pulsed lights has also been proposed in Japanese Patent Application Laid-Open No. 2000-343256. Japanese Patent Application Laid-Open No. 2000-343256 discloses a method for adjusting the emission timings of two pulsed lights by changing a start timing of a pulse laser oscillation.

CITATION LIST

Patent Literature

[PTL 1]
Japanese Patent Application Laid-Open No. 2010-017426

[PTL 2]
Japanese Patent Application Laid-Open No. 2000-343256

SUMMARY OF THE INVENTION

Pulsed light sources have individual differences and are subject to aged deterioration. Therefore even if a control signal is transmitted to a plurality of light sources to irradiate a pulsed light at a same timing, the irradiation timings may actually be discrepant. If the timings of a plurality of pulsed lights irradiated onto a subject are discrepant, a plurality of photoacoustic waves are generated from a same location in the subject, and an artifact is generated on a diagnostic image.

It is possible to change the oscillation start timings of the two pulse lasers, as disclosed in Japanese Patent Application Laid-Open No. 2000-343256, in order to decrease artifacts. In this case however, energy to be stored in the laser medium fluctuates, and the quantity of light in each pulse emission fluctuates. Therefore in the case of a measuring apparatus which generates a diagnostic image using a photoacoustic wave generated by irradiating a plurality of pulsed lights for a plurality of times, the diagnostic image may be uneven.

With the foregoing in view, the present invention provides a technology to decrease a discrepancy of the emission timings of light sources, and decrease the artifacts in the diagnostic image in a measuring apparatus having a plurality of light sources.

The present invention provides a measuring apparatus for obtaining information from a subject, using a photoacoustic effect, the apparatus including: a plurality of laser sources for generating pulsed light; a control unit for outputting an excitation start signal that instructs the laser light sources to start excitation, and outputting an oscillation start signal to instruct the laser light sources to start oscillation after a predetermined time has elapsed from the output of the excitation start signal, so as to generate pulsed light from the laser light sources; an acoustic wave receiving unit for receiving an acoustic wave generated in the subject by the irradiation of the pulsed light; and a signal processing unit for generating information from the subject, using a signal which is output from the acoustic wave receiving unit, wherein the plurality of laser sources include a first laser source and a second laser source of which preparation time from the start of the excitation to the generation of the pulsed light is longer than that of the first laser source, and the control unit sets timing to output the excitation start signal to the first laser source to follow timing to output the excitation start signal to the second laser source according to a difference of the preparation time between the first laser source and the second laser source.

According to the present invention, image quality can be improved by decreasing the discrepancy of emission timings among light sources, and decreasing the artifacts in the diagnostic image.

Further features of the present invention will become apparent from the following description of exemplary embodiments with reference to the attached drawings.

BRIEF DESCRIPTION OF DRAWINGS

FIG. 1 is a block diagram depicting first example of the present invention.
FIG. 2 is a flow chart according to first example of the present invention.

FIG. 3 is a block diagram depicting a control signal generation circuit according to first example of the present invention.
FIG. 4 is a timing chart according to first example of the present invention.
FIG. 5 is a flow chart of an emission timing adjustment processing according to first example of the present invention.
FIG. 6A shows an example of a photoacoustic signal waveform according to first example of the present invention.
FIG. 6B shows an example of a diagnostic image according to first example of the present invention.
FIG. 7 is a flow chart according to second example of the present invention.
FIG. 8 is a block diagram according to third example of the present invention.
FIG. 9 is a flow chart of an emission timing adjustment processing according to third example of the present invention.
FIG. 10 is a timing chart according to third example of the present invention.
FIG. 11A shows an example of a photoacoustic signal waveform according to third example of the present invention.
FIG. 11B shows an example of a diagnostic image according to third example of the present invention.
FIG. 12A shows an example of a conventional measuring apparatus.
FIG. 12B shows an example of a photoacoustic signal waveform of a conventional measuring apparatus.
FIG. 12C shows an example of a diagnostic image of a conventional measuring apparatus.

DESCRIPTION OF EMBODIMENTS

FIRST EXAMPLE (General Configuration)

Figure 1:
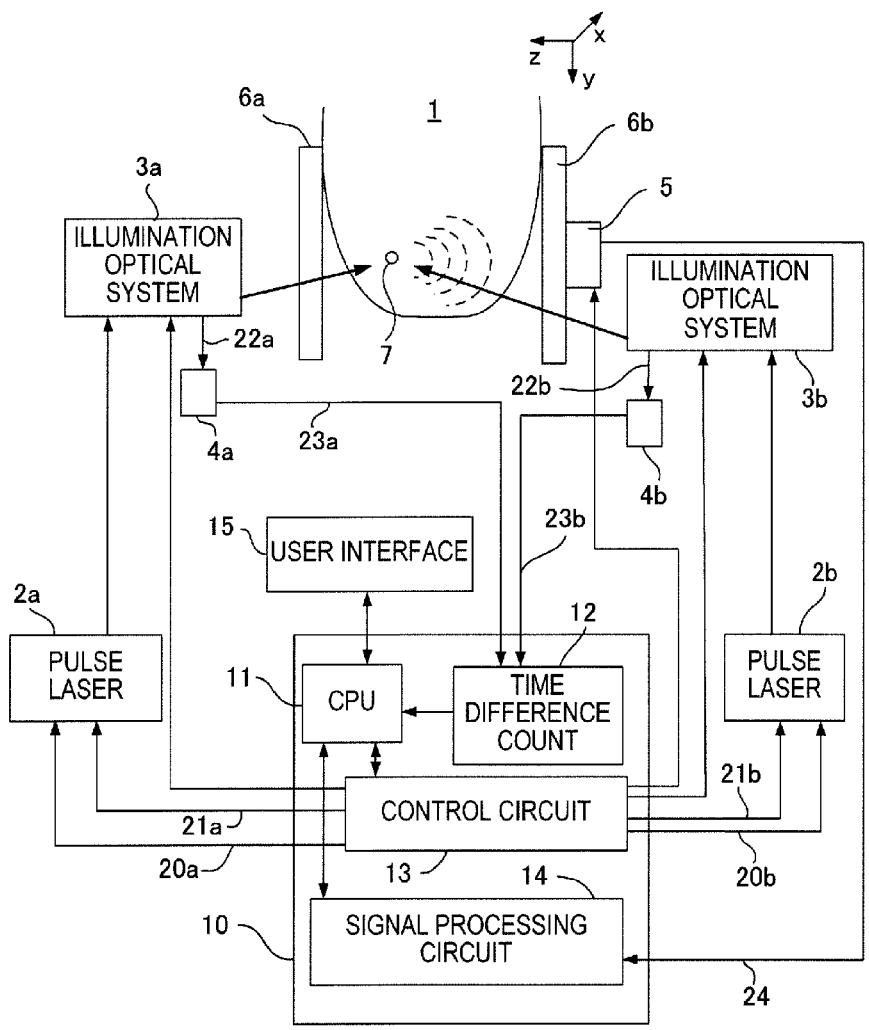
[FIG. 1]

FIG. 1 is a block diagram depicting a first example of a measuring apparatus according to the present invention. In FIG. 1, 1 is a subject and a part of a body of a subject person. For example, if the measuring apparatus is used for the diagnosis of breast cancer, a breast is the subject. This measuring apparatus has a plurality of (two in this example) pulse laser sources 2a and 2b. Hereafter the pulse laser source 2a is also referred to as a first laser source, and the pulse laser source 2b as a second laser source. The pulse laser sources 2a and 2b are light sources for generating pulsed light, and are constituted by a YAG laser, a titanium-sapphire laser or the like. The pulse laser sources 2a and 2b have a flash lamp as a means for exciting the laser medium inside the pulse laser source. Each pulse laser source 2a and 2b has a Q switch. The flash lamp and the Q switch can be externally controlled electrically. If the Q switch is turned ON after turning the flash lamp ON and storing the excitation energy in the laser medium, a pulsed light having high energy, called a giant pulse, is output. The time required from the start of the excitation to the generation of the pulsed light (called "preparation time") depends on the individual difference of the pulse laser source, aged deterioration, model difference or the like. In this example, it is assumed that the preparation time is longer in the pulse laser source 2b than in the pulse laser source 2a.

3a and 3b are illumination optical systems for guiding the pulsed lights generated in the pulse laser sources 2a and 2b to the subject 1, and are constituted by a mirror, beam splitter and shutter or the like. 4a and 4b are optical sensors for detecting a pulsed light, and are constituted by a photo diode and an amplifier circuit respectively. The optical sensors 4a and 4b are disposed in positions where a part of each pulsed light, which passes through the illumination optical systems 3a and 3b, enters respectively. Each of the illumination optical system 3a and 3b reflects the pulsed light using a mirror inside, and guides most of the reflected light to the subject 1, but transmitted light partially exists. This transmitted light enters the optical sensors 4a and 4b.

7 shows an area of which light absorption is high (called the light absorbing area or light absorber) existing inside the subject. If a pulsed light is irradiated onto the light absorbing area 7, a photoacoustic wave is generated due to a photoacoustic effect. The photoacoustic effect is a phenomenon where an acoustic wave is generated from the light absorbing area 7, which expands and contracts by absorbing light energy. This acoustic wave is an elastic wave, such as an ultrasonic wave.

6a and 6b are plate members for compressing and holding the subject 1. The subject 1 is stretched thin by the plate members 6a and 6b, so that the pulsed light can reach inside. 5 is a probe which receives a photoacoustic wave generated inside the subject, and converts the photoacoustic wave into an electric signal (photoacoustic signal). The probe is constituted by a two-dimensional ultrasonic sensor array, for example.

10 is a controller for receiving a photoacoustic signal which is output from the probe 5 and controlling the operation of the pulse laser sources 2a, and 2b, the illumination optical systems 3a and 3b, and the probe 5. The controller 10 encloses a CPU 11, a time difference counting circuit 12, a control circuit 13 and a signal processing circuit 14. The CPU 11 is constituted by a built-in microcomputer and software to control the operation of the entire measuring apparatus. The CPU 11 has an embedded memory, so as to save the setting information of the measuring apparatus.

The time difference counting circuit 12 is a circuit for receiving electric pulse signals from the optical sensors 4a and 4b, and measuring the time difference thereof. This circuit is comprised of a comparison circuit, a counter circuit and a clock generation circuit, and determines the detection of a pulsed light when voltage of the electric pulse signal rises exceeding a predetermined value. The time difference counting circuit 12 activates the counter circuit at each clock cycle, from the rise of one electric pulse signal to the rise of the other electric pulse signal. Then the time difference counting circuit 12 records the sequence of rises of electric pulse signals from the optical sensors 4a and 4b, and the difference of the rise time values between the electric pulse signals.

The control circuit 13 controls a timing of turning ON the flash lamp of each pulse laser source 2a and 2b and a timing of oscillation of the Q switch based on the register values which are set by the CPU 11. The control circuit 13 also controls the switching of the shutter inside the illumination optical system 3a and 3b, and controls whether the pulsed light reaches the subject 1 or not.

The ends of the illumination optical systems 3a and 3b and the probe 5 are attached to an XY stage, which is not illustrated, so as to move relatively with respect to the subject 1. Thereby the pulsed light is irradiated onto and the photoacoustic wave is received from many points on the surface of the subject 1, and photoacoustic signals are obtained from a wide range.

The signal processing circuit 14 is a circuit to receive a photoacoustic signal from the probe 5, and to perform amplification, signal processing and image reconstruction. The signal processing circuit 14 is comprised of an operational amplifier, an A/D converter, and an FPGA among others. 15 is a user interface for a user to control the operation of the measuring apparatus and change settings, and to display diagnostic images to the user. The user interface 15 is comprised of an input device such as a keyboard, and an output device such as a display.

For the control signals to control the pulse laser sources 2a and 2b, an excitation start signal to instruct the start of excitation, and an oscillation start signal to instruct the start of the oscillation are used. The excitation start signal is a control signal for turning ON the flash lamp inside the light source, and the oscillation start signal is a control signal for closing the Q switch and generating a giant pulse by rapid oscillation. Both of these signals are DC 5V digital pulse signals. In FIG. 1, 20a is the excitation start signal for the pulse laser source 2a, and 21a is the oscillation start signal for the pulse laser source 2a. 20b is the excitation start signal for the pulse laser source 2b, and 21b is the oscillation start signal for the pulse laser source 2b.

22a is a pulsed light which enters the illumination optical system 3a to the optical sensor 4a, and 22b is a pulsed light which enters from the illumination optical system 3b to the optical sensor 4b. 23a is an electric pulse signal which is output from the optical sensor 4a, and 23b is an electric pulse signal which is output from the optical sensor 4b. These are analog pulse signals. 24 is a photoacoustic signal which is output from the probe 5.

In this example, the CPU 11 and the control circuit 13 correspond to the control unit of the present invention, the probe 5 corresponds to the acoustic wave receiving unit of the present invention, and the signal processing circuit 10 corresponds to the signal processing unit of the present invention. The optical sensors 4a and 4b and the time difference counting circuit 12 correspond to the detection unit of the present invention, which detects the difference of the pulsed light generation timings.

(Operation Flow)

Figure 2:
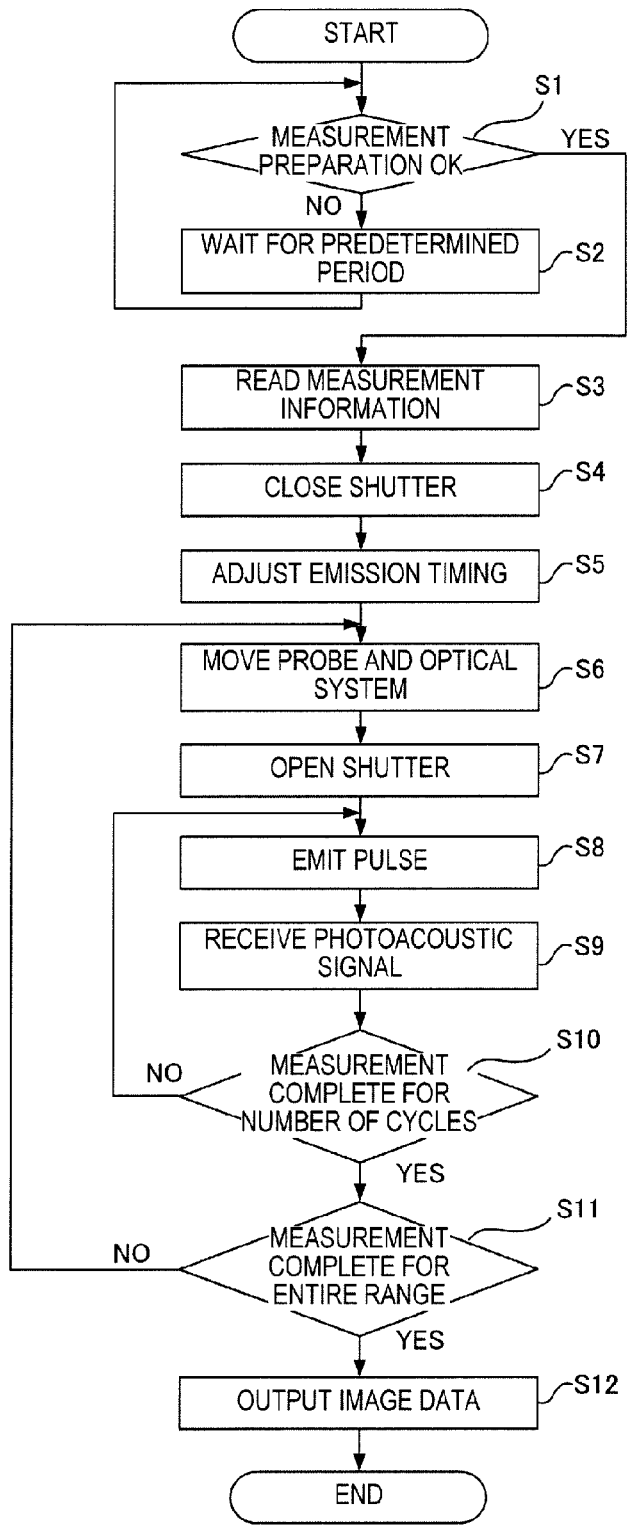
[FIG. 2]

FIG. 2 shows an operation flow of the measuring apparatus to be executed by the controller 10. In step S1, the CPU 11 checks whether the measuring is ready. If the subject 1 is secured between the plate members 6a and 6b, the CPU 11 determines that the measurement is ready, and advances to step S3. If the measurement is not ready, the CPU 11 advances to step S2, waits for a predetermined time, then returns to step S1.

Then in step S3, the CPU 11 reads the setting information, which the user specified via the user interface 15, and records the information to the internal memory. The setting information is, for example, a number of irradiation cycles at a same measurement position, a measurement range and wavelength of a pulsed light.

Then in step S4, the CPU 11 transmits a control signal to close the shutters (light interrupting units) disposed inside the illumination optical systems 3a and 3b via the control unit 13. Thereby the pulsed lights from the pulse laser sources 2a and 2b enter the optical sensors 4a and 4b respectively, but do not reach the subject 1. Then in step S5, the CPU 11 adjusts the timings of the control signals for the pulse laser sources 2a and 2b via the control unit 13. The method for adjusting the timings will be described later.

In step S6, the CPU 11 drives the XY stage via the control unit 13, and moves the ends of the illumination optical systems 3a and 3b and the probe 5 to the measurement position of the subject 1. Then in step S7, the CPU 11 transmits a control signal to open the shutters disposed inside the illumination optical systems 3a and 3b respectively via the control circuit 13. Thereby the pulsed lights from the pulse laser sources 2a and 2b can reach the optical sensors 4a and 4b and the subject 1 respectively.

Then in step S8, the CPU 11 transmits a control signal to the pulse laser sources 2a and 2b via the control circuit 13 to generate pulsed lights. The control circuit 13 rises the excitation start signals and the oscillation start signals of the pulse laser sources 2a and 2b at the timings adjusted in step S5. As a result, the plurality of pulsed lights can be irradiated onto the subject 1 almost at the same time, regardless the individual difference of the plurality of pulse laser sources.

The photoacoustic wave generated inside the subject 1 is converted into an electric signal by the probe 5, and is transferred to the signal processing circuit 14. In step S9, the signal processing circuit 14 inputs the photoacoustic signals for a predetermined time, and stores the signals in the internal memory after the electric pulse signal from the optical sensor 4a or 4b rises. In this case, signals generated at a same position on the subject are arithmetic averaged to decrease the influence of noise.

Then in step S10, the CPU 11 determines whether a number of times of saving the photoacoustic signals into the internal memory reached the number of irradiation cycles read in step S3. Processing advances to step S11 if the read value is reached, and returns to step S8 if not reached. For example, if a value 3 is read in step S3 as the number of irradiation cycles, the processing in step S8 and step S9 is repeated three times, and then processing advances to step S11.

Then in step S11, the CPU 11 determines whether measurement is completed for the entire measurement range of the subject 1. The measurement range was read in step S3. If measurement is completed for the entire measurement range, processing advances to step S12. If there are positions where measurement is not completed, processing returns to step S6 and continues. In step S12, the CPU 11 reconstructs the image based on the photoacoustic signal data at each measurement position stored in the internal memory of the signal processing circuit 14, and outputs the diagnostic image, to indicate the spectral characteristics inside the subject 1, to the user interface 15.

(Control Signal Generation Circuit)

Figure 3:
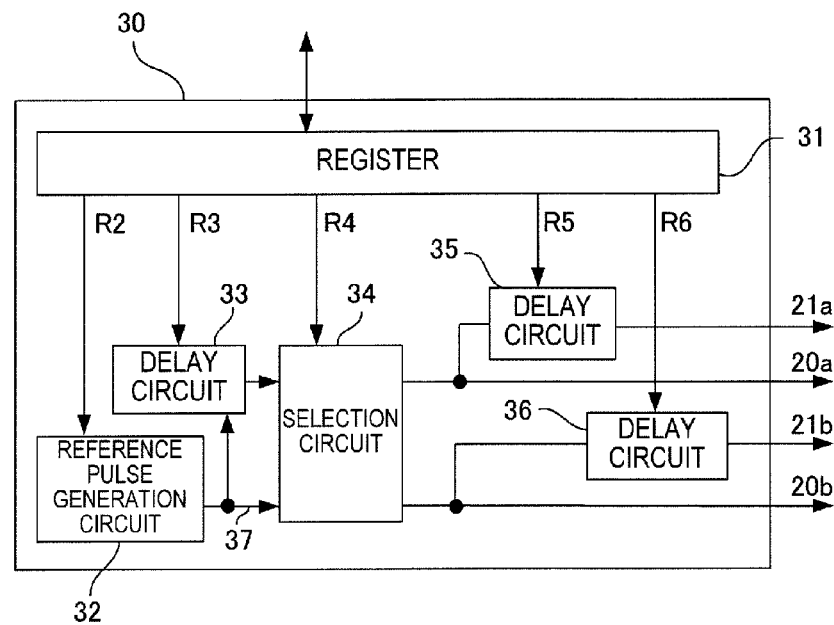
[FIG. 3]

FIG. 3 is a block diagram of a portion of generating control signals 20a, 21a, 20b and 21b to the pulse laser sources 2a and 2b among the internal circuits of the control circuit 13.

In FIG. 3, 30 is a generation circuit for generating the control signals 20a, 21a, 20b and 21b to the pulse laser sources 2a and 2b. The generation circuit 30 is a logic circuit implemented on a device, such as an FPGA. 31 is a register which is read or written by the CPU 11. The register 31 has five registers (R2 to R6). R2 is a control register which starts operation of the generation circuit 30. R3 is an excitation delay setting register which sets the delay time in a delay circuit 33. R4 is a selection setting register which sets an operation of a selection circuit 34. R5 is an oscillation delay setting register for the pulse laser source 2a which sets the delay time in a delay circuit 35. R6 is an oscillation delay setting register for the pulse laser source 2b which sets the delay time in a delay circuit 36. 32 is a reference pulse generation circuit which outputs a reference pulse signal 37 to the delay circuit 33 and the selection circuit 34 at a predetermined frequency when the value of the control register R2 is 1. In this example, it is assumed that the frequency of the reference pulse signal 37 is 10 Hz, and the pulse laser sources 2a and 2b can output pulsed lights at a 10 Hz frequency.

The delay circuit 33 is a circuit which delays the reference pulse signal 37 for the time specified by the excitation delay setting register R3, and outputs it to the selection circuit 34. The unit of time is nano seconds. For example, if the set value of the excitation delay setting register R3 is 2000, the delay circuit 33 delays the reference pulse signal 37 for 2 micro seconds, and outputs it.

The selection circuit 34 is a circuit which inputs the reference pulse signal 37 and the delayed pulse signal output from the delay circuit 33, and outputs the excitation start signals 20a and 20b according to the value of the selection setting register R4. The selection setting register R4 can take four values, 0 to 3. If the value of the selection setting register R4 is 0, the reference pulse signal 37 is output for the excitation start signal 20a, and the output signal from the delay circuit 33 is output for the excitation start signal 20b. If the value of the selection setting register R4 is 1, the reference pulse signal 37 is output for the excitation start signal 20b, and the output signal from the delay circuit 33 is output for the excitation start signal 20a. If the value of the selection setting register R4 is 2, the reference pulse signal 37 is output for the excitation start signal 20a, and no pulse signal is output for the excitation start signal 20b. If the value of the selection setting register R4 is 3, the reference pulse signal 37 is output for the excitation start signal 20b, and no pulse signal is output for the excitation start signal 20a.

The delay circuit 35 is a circuit which delays the excitation start signal 20a for the time specified by the oscillation delay setting register R5 for the pulse laser source 2a, and outputs the result as the oscillation start signal 21a. The unit of the time is assumed to be nano seconds. The delay circuit 36 delays the excitation start signal 20b for the time (nano seconds) specified by the oscillation delay setting register R6 for the pulse laser source 2b, and outputs the result as the oscillation start signal 21b.

In this way, the timings of the excitation start signals 20a and 20b and the oscillation start signals 21a and 21b can be flexibly changed at high precision, by providing the delay circuits 33, 35 and 36 as hardware inside the control circuit 13, and allowing to change settings thereof via the user interface 15. If both the pulse laser sources 2a and 2b are emitted, the pulse laser source to be excited first in time can be changed by changing the value of the selection setting register R4 to 0 or 1. Operation to emit only one of the pulsed laser sources 2a and 2b can also be implemented by changing the value of the selection setting register R4 to 2 or 3. Hereafter an operation in the case of emitting both the pulse laser sources 2a and 2b will be described.

(Emission Timing Adjustment)

The processing the CPU 11 performs during the emission timing adjustment processing in step S5 in FIG. 2 will now be described with reference to FIG. 4 and FIG. 5.

Figure 4:
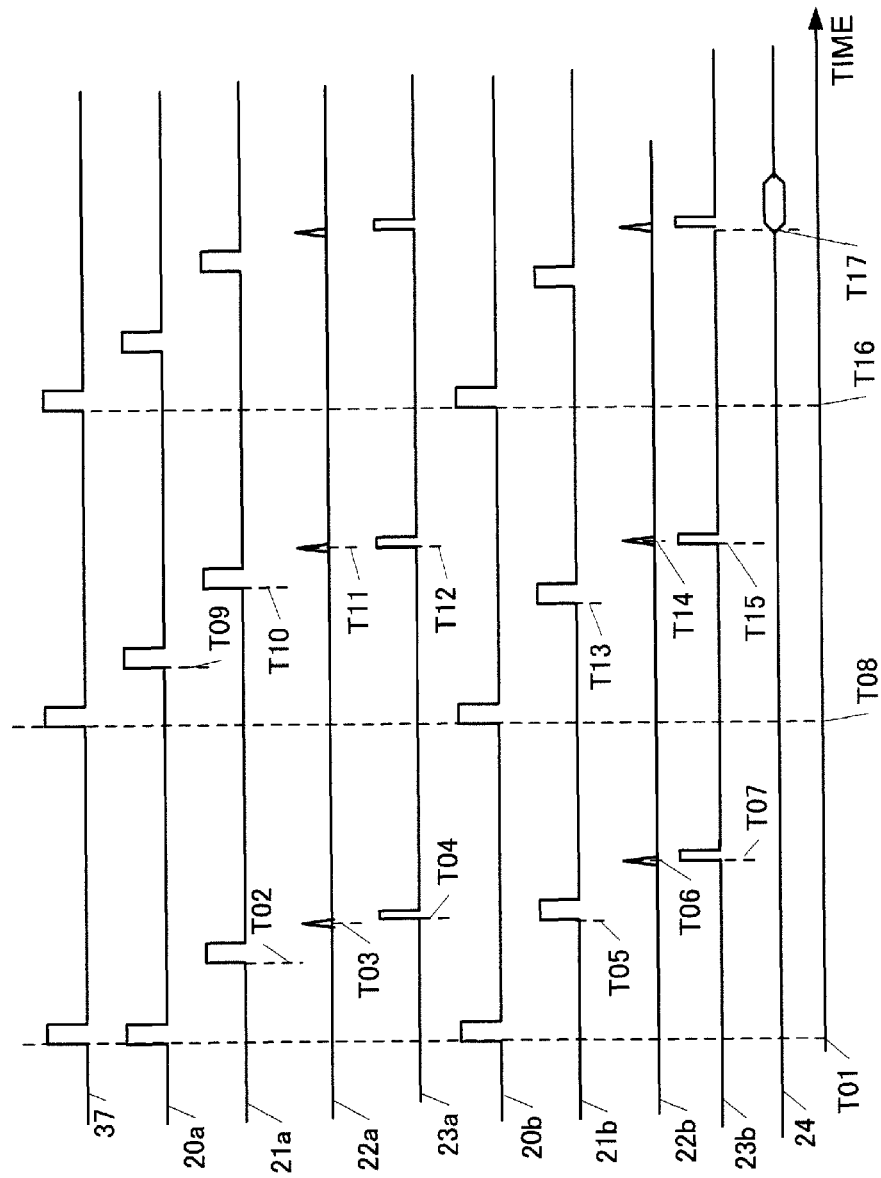
[FIG. 4]
Figure 5:
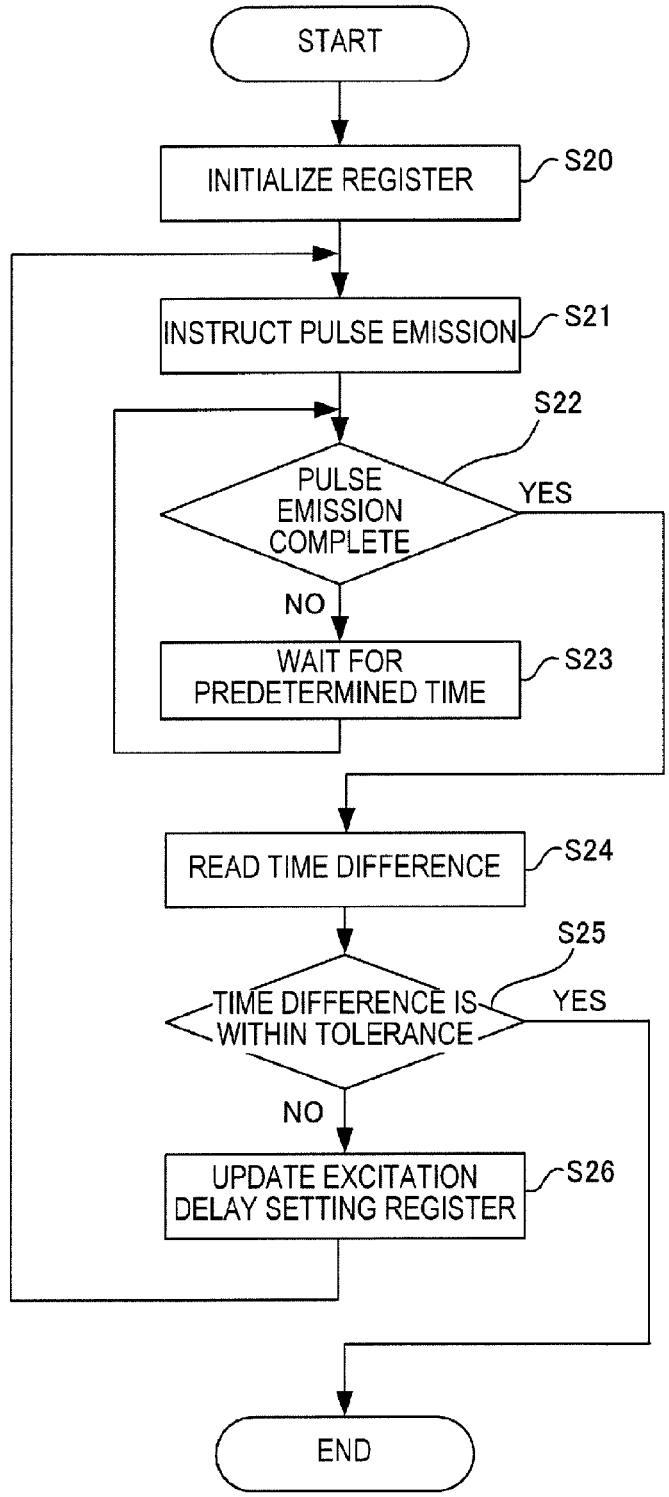
[FIG. 5]

FIG. 4 is a time chart depicting a relationship of the control signals 20a, 21a, 20b and 21b to the pulse laser sources 2a and 2b, pulsed lights 22a and 22b, electric pulse signals 23a and 23b and the photoacoustic signal 24. FIG. 5 is a flow chart showing details of the emission timing adjustment processing which the CPU 11 executes in step S5.

In step S20, the CPU 11 initializes the values of the registers R2 to R6 described in FIG. 3. Here the values of the control register R2, the excitation delay setting register R3 and the selection setting register R4 are set to 0. The CPU 11 also sets the oscillation delay setting register R5 for the pulse laser source 2a and the oscillation delay setting register R6 for the pulse laser source 2b to pre-adjusted initial values. It is assumed that optimum values are determined based on the power consumption and quantity of the pulsed light when the pulse laser sources 2a and 2b are setup. In the description here, it is assumed that the value of the oscillation delay setting register R5 for the pulse laser source 2a is set to 150000, and the oscillation delay setting register R6 for the pulse laser source 2a is set to 152000, for example. The value of the oscillation delay setting register R5 for the pulse laser source 2a determines the time for storing energy in the laser medium of the pulsed laser source 2a (excitation time), and is closely related to the light quantity of the pulsed light 22a. The same for the oscillation delay setting register R6 for pulse laser source 2b, which is closely related to the light quantity of the pulsed light 22b. It is assumed that these values are predetermined depending on the size of the target light absorbing area 7 and the quantity of light that can be irradiated onto the subject 1, and held in the memory of the CPU 11.

Then in step S21, the CPU 11 sets the value of the control register R2 to 1. Thereby the reference pulse signal 37 starts to be output from the reference pulse generation circuit 32 at a 10 Hz frequency (time T01).

At first, the value of the excitation delay setting register R3 is initialized to 0, hence the output signal from the delay circuit 33 is also output at the same time with the reference pulse signal 37. The value of the selection setting register R4 is also initialized to 0, hence the excitation start signals 20a and 20b are output at the same timing. Thereby the flash lamps inside the pulse laser source 2a and 2b turn ON, energy of the laser medium is stored, and the excitation state is established. On the other hand, the value of the oscillation delay setting register R5 for the pulse laser source 2a is set to 150000, hence, the oscillation start signal 21a is output when 150 micro seconds elapsed after the excitation start signal 20a (time T02). Due to this, the Q switch is turned ON in the pulse laser source 2a, the rapid amplification and the oscillation of the excitation energy occur, and the pulsed light 22a is output at several 100 nano seconds later (time T03). This timing is different depending on the pulse laser source and the wave length set value. The electric pulse signal 23a is output after several nano seconds of delay in the optical sensor 4a (time T04).

On the other hand, the value of the oscillation delay setting register R6 for the pulse laser source 2b is set to 152000, so the oscillation start signal 21b is output when 152 micro seconds elapsed after the excitation start signal 20b (time T05). Thereby the Q switch turns ON in the pulse laser source 2b, and rapid amplification and the oscillation of excitation energy occur. Then the pulsed light 22b is output several 100 nano seconds later (time T06). After several nano seconds of delay in the optical sensor 4b, the electric pulse signal 23b is output (time T07).

The difference of rise time between the electric pulse signals 23a and 23b, that is, the value of "T07–T04" is measured and recorded by the time difference counting circuit 12 in nano second units. This time difference corresponds to the difference of the pulsed light generation timings between the two pulse laser sources 2a and 2b. Here it is assumed that if the electric pulse signal 23a rises before the electric pulse signal 23b, a positive value is recorded. For example, if the electric pulse signal 23a rises and then the electric pulse signal 23b rises at 2.2 micro second later, 2200 [ns] is recorded as the time difference "T07−T04". If the electric pulse signal 23b rises and then the electric signal 23a rises at 2.2 micro seconds later, a −2200 [ns] is recorded as the time difference "T07−T04".

The CPU 11 enters the wait state during a period from time T01 to time T07. In step S22, the CPU 11 accesses the time difference counting circuit 12 and determines whether the measurement of the time difference of the electric pulse signals 23a and 23b corresponding to the pulsed lights 22a and 22b generated in step S21 has completed. If completed, processing advances to step S24. If not completed, processing advances to step S23, and returns to step S22 after waiting for a predetermined time.

In step S24, the CPU 11 accesses the time difference counting circuit 12 and reads the value "T07−T04" as the time difference.

In step S25, the CPU 11 compares the time difference "T07−T04" with the tolerance of the timing discrepancy of the pulsed light, and determines whether the time difference is within the tolerance. It is assumed that this tolerance is determined in advance depending on the pulse widths of the pulsed light 22a and the pulsed light 22b, the frequency characteristics of the probe 5 and the like, and stored in the CPU 11. The generation timings of the two pulsed lights 22a and 22b need not be exactly the same. It is sufficient only if the photoacoustic wave is not generated twice from one light absorbing area, therefore it is acceptable if the discrepancy of the generation timings is smaller than the width of the pulsed light, and the two pulsed lights overlap in the time direction. In the present example, a case of the time difference "T07−T04" is 2200 [ns] will be described as an example. In this example, the width of the pulsed light is approximately 10 [ns], and the tolerance is determined to be −10 [ns] or more 10 [ns] or less, so that the two pulsed lights overlap.

If the time difference "T07−T04" is within the tolerance, the CPU 11 determines that the generation timings of the two pulsed lights match, and ends the processing. In this case, the CPU 11 may write 0 in the control register so as to stop the reference pulse signal 37 once. If the time difference "T07−T04" is outside the tolerance, processing advances to step S26.

In step S26, the CPU 11 changes the setting of the control circuit 13 so that the time difference, measured by the time difference counting circuit 12, is cancelled. The CPU 11 writes the absolute value of the time difference (T07−T04) read in step S24 to the excitation delay setting register R3. If the value of "T07−T04" is 0 or more, the CPU 11 writes 1 to the selection setting register R4. If the value of "T07−T04" is negative, the CPU 11 writes 0 to the selection setting register R4. If the value of "T07−T04" is 2200, for example, the CPU 11 sets 2200 in the excitation delay setting register R3, and writes 1 to the selection setting register R4.

Then processing returns to S21 and the CPU 11 continues processing. In this case, the reference pulse signal 37 is output at time T08, which is 100 milli seconds after time T01. If the value of the excitation delay setting register R3 is 2200, a pulse signal is output from the delay circuit 33 at 2.2 micro seconds after time T08 (time T09). Since the value of the selection setting register R4 is 1, a pulse signal is output at time T09 for the excitation start signal 20a, and a pulse signal is output at time T08 for the excitation start signal 20b. In other words, the flash lamp of the pulse laser source 2a starts to turn ON at 2.2 micro seconds after the flash lamp of the pulse laser source 2b turns ON.

The value of the oscillation delay setting register R5 for the pulse laser source 2a is not changed in step S26. This means that the time difference "T10−T09" of the oscillation start signal 21a and the excitation start signal 20a remains at 150 micro seconds. If a pulse signal is output for the oscillation start signal 21a at time T10, the Q switch turns ON in the pulse laser source 2a, and rapid amplification and oscillation of the excitation energy occur. Then the pulsed light 22a is output in at several 100 nano seconds later (time T11). After several nano seconds of delay in the optical sensor 4a, the electric pulse signal 23a is output (time T12).

On the other hand, the value of the oscillation delay setting register R6 for the pulse laser source 2b is not changed in step S26 either. This means that the time difference "T13−T08" of the oscillation start signal 21b and the excitation start signal 20b remains at 152 micro seconds. If a pulse signal is output for the oscillation start signal 21b at time T13, the Q switch turns ON in the pulse laser source 2b, and rapid amplification and oscillation of the excitation energy occur, and the pulsed light 22b is output at several 100 nano seconds later (time T14). After several nano seconds of delay in the optical sensor 4b, the electric pulse signal 23b is output (time T15).

By measuring the time difference due to the individual difference of the light source and the aged deterioration at the first emission, and shifting the start of the second excitation, the time difference "T15−T12" of the electric pulse signal 23a and the electric pulse signal 23b, that is the discrepancy of the emission timings, can be minimized. The fluctuation of the pulsed light quantity in each emission is decreased by keeping the time difference "T10−T09" and "T13−T08", between the excitation start and the oscillation start, constant.

If the time difference between the electric pulse signal 23a and the electric pulse signal 23b becomes within the tolerance by the timing control thus far, the emission timing adjustment processing ends. Then irradiation of the pulsed light onto the subject and reception of the photoacoustic wave are started by the processing in step S6 and later in FIG. 2 (time T16). Since the CPU 11 does not change the register value in the control circuit 13 here, the pulse laser sources are controlled at the same timings from time T08 to time T16. The reception of the photoacoustic signal starts synchronizing with the electric pulse signal 23a or the electric pulse signal 23b (time T17).

(Comparison with Prior Art)

Figure 12A:
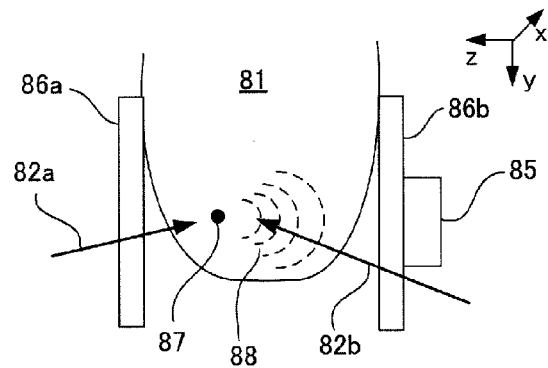
[FIG. 12A]
Figure 12B:
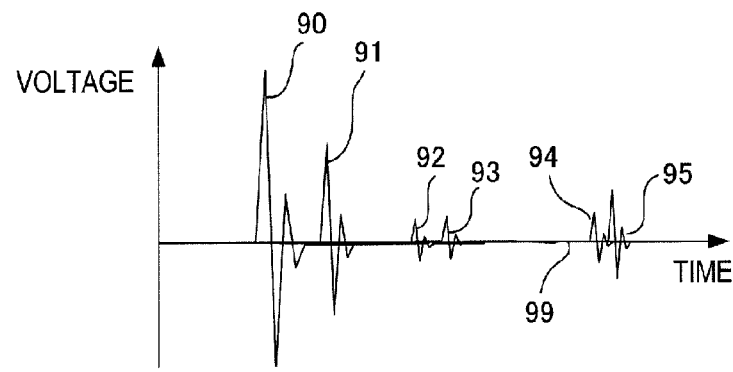
[FIG. 12B]
Figure 12C:
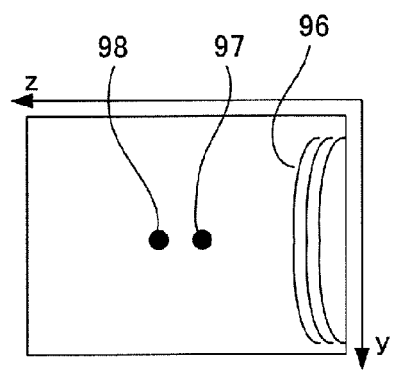
[FIG. 12C]

After describing the problems of a conventional measuring apparatus with reference to FIG. 12A to FIG. 12C, the advantages of this example will be described. FIG. 12B is an example of the photoacoustic signal which is output from a probe 85 of a conventional measuring apparatus shown in FIG. 12A. The abscissa indicates time, and the ordinate indicates voltage. FIG. 12C is an example of a diagnostic image created by converting the photoacoustic signal by the conventional measuring apparatus.

The emission timing and the light quantity of a pulse laser source fluctuates depending on the individual difference and the aged deterioration of the light source, or the wavelength of the pulsed light. If such a discrepancy of emission timings and discrepancy of light quantity are generated, an artifact is generated on the diagnostic image, and image quality drops.

First an artifact, due to the discrepancy of timings of pulsed lights 82a and 82b, will be described. If the timings of the two pulsed lights 82a and 82b are discrepant, a photoacoustic wave 88 is generated twice from one light absorbing area 87. Since these photoacoustic waves reach the probe 85 at different timings, photoacoustic signals 92 and 93 are output from the probe 85 at two separate times. If such photoacoustic signals are received, a signal processing circuit misjudges that two light absorbing areas exist at different positions.

Hence the light absorbing area, which is at one location, is displayed as two separate images, 97 and 98, in the diagnostic image.

An artifact due to the discrepancy of light quantity will be described next. When the pulsed light 82b is irradiated onto the subject 81, a part thereof is absorbed by the surfaces of a plate member 86b and the subject 81, and the photoacoustic waves are generated. Signals 90 and 91 generated by the photoacoustic waves are output first. If the quantity of the pulsed light 82b is too high, a strong photoacoustic wave is generated, and is reflected multiple times between the plate member 86b and the subject 81, hence the noise signals 90 and 91 are generated for a long time. As a result, an artifact 96 is generated in the diagnostic image. If the light quantity of the pulsed lights 82a and 82b is too low, on the other hand, the photoacoustic wave 88 from the light absorbing area 87 becomes weak, and the images 97 and 98 in the diagnostic image blur.

When the pulsed light 82a is irradiated onto the subject 81, a part thereof is absorbed by the surfaces of a plate member 86a and the subject 81, and photoacoustic waves are generated. However signals 94 and 95 generated by these photoacoustic waves are output last, and the influence on the diagnostic image can be prevented by not using the signals after time 99 for generating a diagnostic image.

Figure 6A:
[FIG. 6A]
Figure 6B:
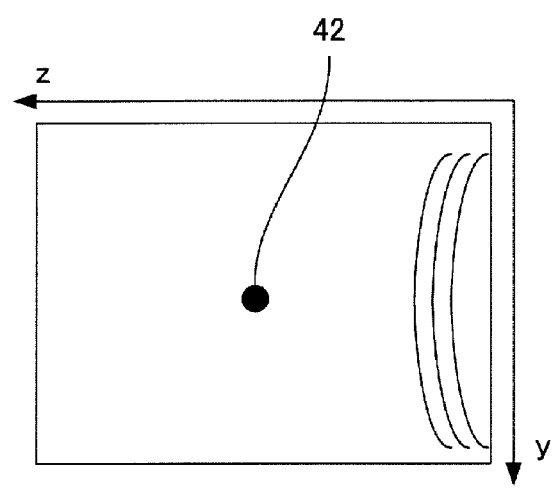
[FIG. 6B]

Now an example of a photoacoustic signal waveform and a diagnostic image according to this example is shown in FIG. 6A and FIG. 6B. FIG. 6A is an example of the photoacoustic signal which is output from the probe. The abscissa indicates time, and the ordinate indicates voltage. FIG. 6B is a diagnostic image created by converting the photoacoustic signal.

According to this example, the pulsed lights 22a and 22b are irradiated onto the subject 1 almost simultaneously at time T17. Due to this, the photoacoustic wave is generated only once from the light absorbing area 7. Therefore corresponding the photoacoustic signal 41 and an image 42 in the diagnostic image are integrated into one. Since the energy of the two pulsed lights are simultaneously absorbed by the light absorbing areas 7, a stronger photoacoustic wave is generated compared with the case of pulsed lights of which timings are discrepant. As a result, the voltage of the photoacoustic signal 41 is higher than those of the photoacoustic signals 92 and 93 measured by a conventional apparatus. It is also possible to enhance the contrast of the image 42 in the diagnostic image by this example, compared with those of images 97 and 98 in the case of the pulsed lights of which timings are discrepant.

(Variant Form)

In this example, a case of irradiating pulsed lights of the two pulse laser sources 2a and 2b from positions opposite the subject 1 was described for simplification, but a number of pulse laser sources may be three or more. The irradiating direction is not limited to the direction opposite the subject 1. For example, the present invention can be applied to a case of disposing many illumination optical systems around the subject, and irradiating pulsed lights simultaneously from many directions.

In this example, a case of two identical pulse laser sources 2a and 2b was described, but the present invention can also be applied to a case of a plurality of pulse laser sources of which types are different. In this case, the discrepancy of timings of the pulsed lights, not only due to the individual difference of the pulsed laser sources, but also due to the difference of types of the plurality of pulse laser sources, can be prevented.

In FIG. 2 of this example, a case of adjusting the timings of the pulse laser sources after the measurement of the subject 1 is ready was described, but the sequence of the timing adjustment and other processing is not limited to this. For example, the subject 1 may be secured to the measurement position after the timing adjustment is performed first. In this case, the time of binding the subject 1 can be decreased, and burden on the subject person can be decreased.

If the pulse laser sources 2a and 2b allow the user to set the wavelength, frequency, energy to be supplied and the like, the timing may be adjusted every time the setting of the pulse laser sources 2a and 2b is changed.

To deal with aged deterioration of the pulse laser sources, timing may be adjusted when the apparatus is started up or at a predetermined time, such as every morning. The time difference measured by the time difference counting circuit 12 may be constantly monitored by the CPU 11, so that the timing is adjusted when the timing difference is outside the tolerance. The CPU 11 may store an accumulated emission count of the pulsed lights from the pulse laser sources 2a and 2b, and may adjust the timing when the count reaches a predetermined value.

In the present example, an individual difference of the delay from the emission of the pulsed light to the rise of the electric pulse signal, which the optical sensors 4a and 4b generate, is ignored, but the present invention is not limited to this. If the individual difference of delay is measured for the optical sensors 4a and 4b in advance and is reflected in the value of the excitation delay setting register, then the timing discrepancy of the pulsed lights irradiated onto the subject 1 can be decreased.

In this example, a case of generating the reference pulse signal 37 in the reference pulse generation circuit at a predetermined cycle was shown, but the method of generating the reference pulse signal is not limited to this, and the reference pulse signal may be generated synchronizing with another control signal. For example, the time difference "T12–T08" between the reference pulse signal generation and the electric pulse signal generation is stored when the emission timing is adjusted. The moving velocity of the probe 5 is assumed to be V in step S6. The reference pulse signal 37 is generated at a timing when the probe 5 passes a position at "V×(T12–T08)" before the measurement position. When time "T12–T08" elapses after the generation of the reference pulse signal 37, the pulsed lights 22a and 22b are emitted. By this timing, the probe 5 advances "V×(T12–T08)", and has passed the area near the measurement position.

By synchronizing the reference pulse signal 37 with the position information of this probe 5 like this when the measurement is performed while moving the probe 5, the pulsed light can be emitted at the same timing reaching the measurement position, and the positional accuracy of the measurement can be increased.

As described above, according to first example of the present invention, the starts of the flash lamps turning ON are shifted based on the timing discrepancy of the plurality of pulsed lights, and the interval between the oscillation start of the Q switch and the start of the flash lamp turning ON is kept constant. Thereby a plurality of timings of pulse emission is aligned while suppressing the fluctuation of light quantity. As a result, a phenomenon where a plurality of photoacoustic waves are generated from a same area in the biological tissue, and an artifact is generated in the diagnostic image, can be prevented.

SECOND EXAMPLE

Second example of the present invention will be described next. A difference of Second example from first example is that a timing is also adjusted when measuring a subject. This example is for supporting a case when the fluctuation of the emission timing is gradually increasing when pulsed light is irradiated onto the subject, due to the temperature rise inside the pulse laser source.

Description on the block diagram in FIG. 1 and the control signal generation circuit 30 in FIG. 3 is omitted since both are already described in first example.

Figure 7:
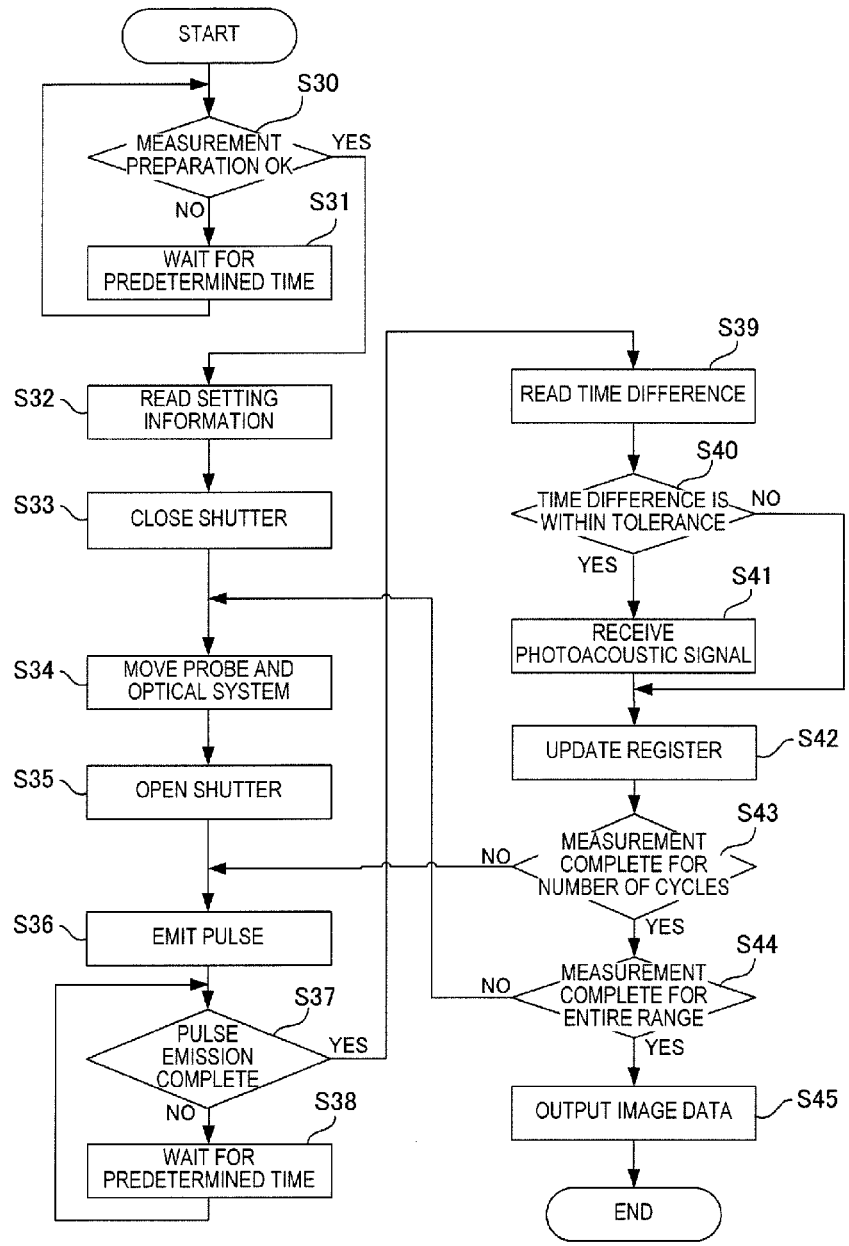
[FIG. 7]

An operation flow of a measuring apparatus of this example will now be described with reference to FIG. 7. Description on step S30 to step S33, which is the same as step S1 to step S4 in first example, is omitted. It is assumed that the values in the previous measurement are held in the register 31 in the control circuit 13 when step S33 is completed. Description on step S34 to step S36, which is the same as step S6 to step S8 in first example, is omitted.

Description on step S37 to step S40, which is the same as step S22 to step S25 in first example, is omitted.

In step S40, if the time difference between the electric pulse signal 23a and the electric pulse signal 23b is within the tolerance, it is determined that the timings of the pulsed lights are matched, and processing advances to step S41. If this time difference is outside the tolerance, processing advances to step S42. Description on step S41 and step S42, which is the same as step S9 and step S26 in first example, is omitted. Description on step S43 to step S45, which is the same as step S10 to step S12 in first example, is omitted.

As described above, according to second example of the present invention, the value of the excitation delay setting register R3 is updated every time the pulsed light is emitted when measuring a subject. Thereby the discrepancy of the timings of the pulsed lights 22a and 22b during measurement can be decreased. As a result, even if temperature rises during measurement and the characteristics of the pulse laser sources change, the generation of an artifact can be prevented. If the discrepancy of the pulsed lights is outside the tolerance in step S40, the acoustic signal data is not obtained in step S41, therefore even if a discrepancy of timings of the pulsed lights is unexpectedly generated during the measurement, the generation of an artifact on the diagnostic image can be prevented.

THIRD EXAMPLE

Third example of the present invention will be described next. A difference of third example from first example is that not only a timing of turning ON the flash lamp of the pulse laser sources, but also the interval from the turning ON the flash lamp to the oscillation of the Q switch is changed. By changing the interval from the lighting of the flash lamp to the oscillation of the Q switch, the quantity of the energy to be stored in the laser medium inside the pulse laser source is changed. This example allows to adjust the pulsed light to be irradiated onto the subject 1. For example, in FIG. 1, a strong photoacoustic wave may be generated from the surface of the plate member 6b in some cases when the quantity of pulsed light from the illumination optical system 3b is too strong. In this case, the photoacoustic wave, not from the subject 1, wraps around the probe 5, which may generate an artifact. A case of decreasing the quantity of pulsed light from the illumination optical system 3b to decreased this artifact, so that the quantity of pulsed light from the illumination optical system 3a is increased for the amount of the above decrease, will be described.

Figure 8:
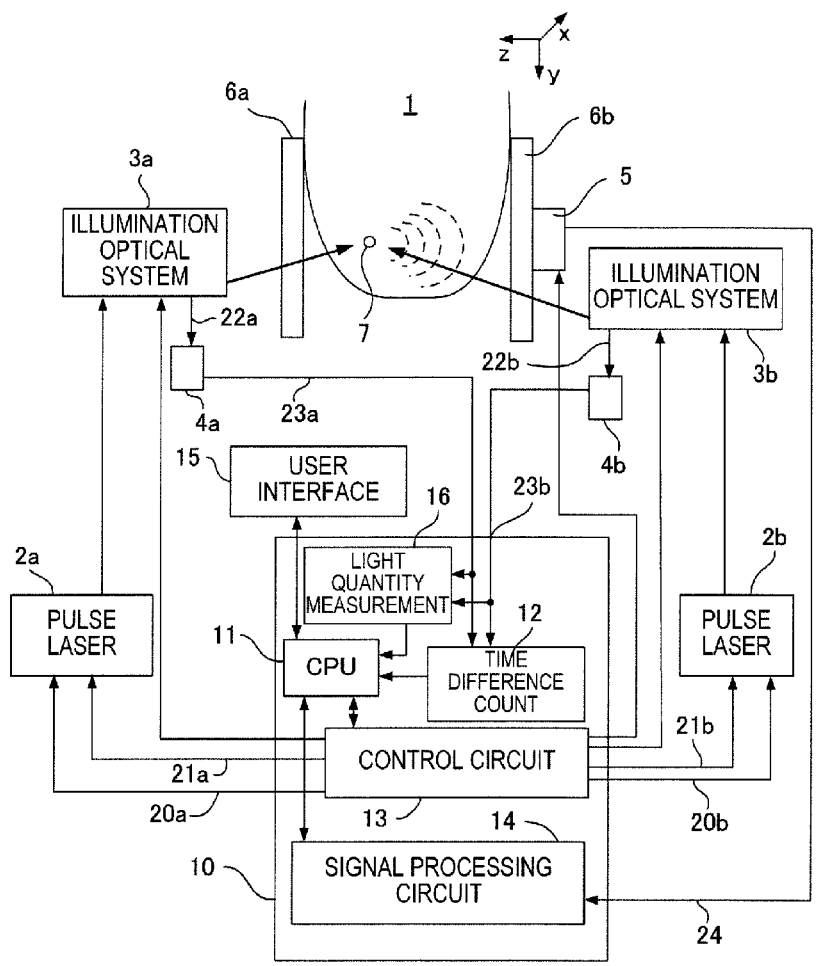
[FIG. 8]

Description on the block diagram in FIG. 8, which is the same as that of first example except for the light quantity measuring circuit 16, is omitted. The light quantity measuring circuit 16 is a circuit for measuring the quantity of pulsed light using electric pulse signals 23a and 23b from optical sensors 4a and 4b. The light quantity measuring circuit 16 integrates the electric pulse signals 23a and 23b for each pulse emission, determines the intensity values of the pulsed light 22a and 22b, and stores these values in an internal register.

Figure 9:
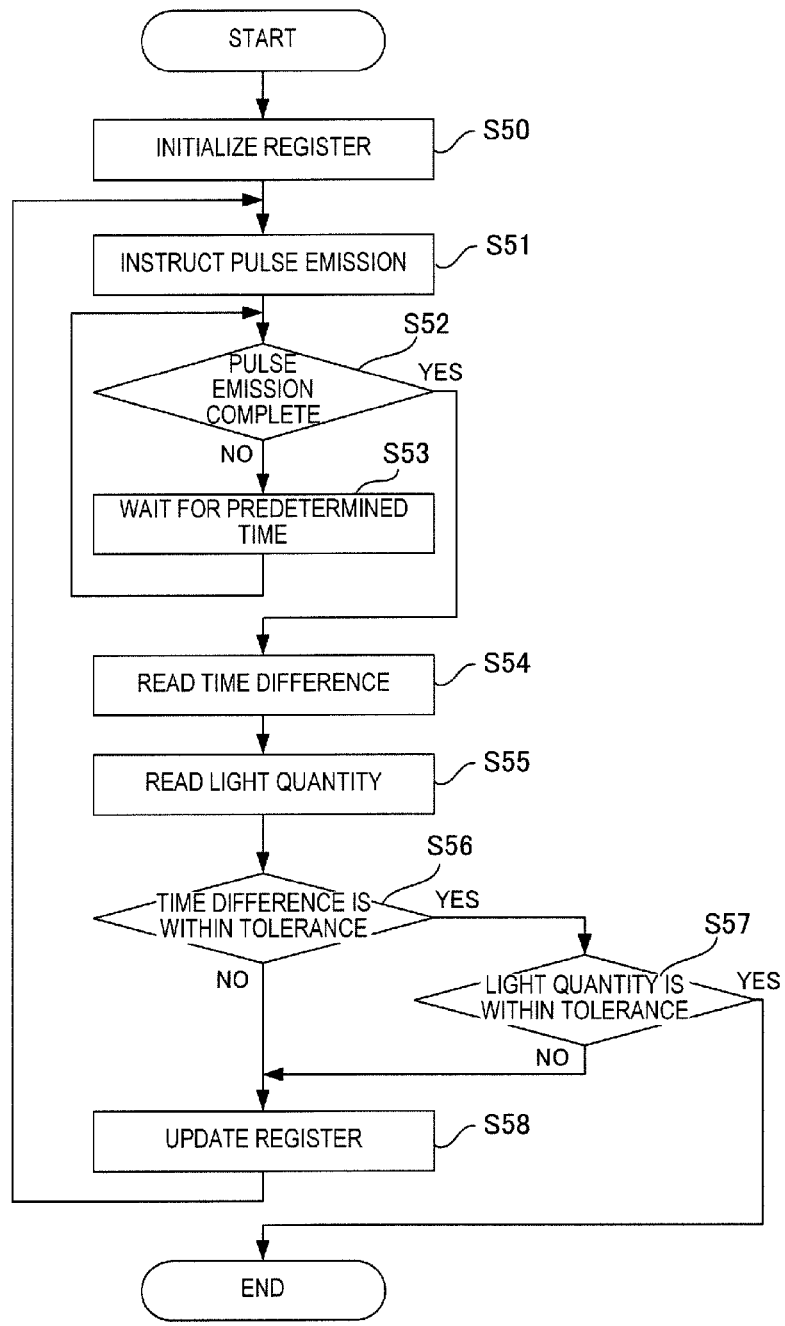
[FIG. 9]
Figure 10:
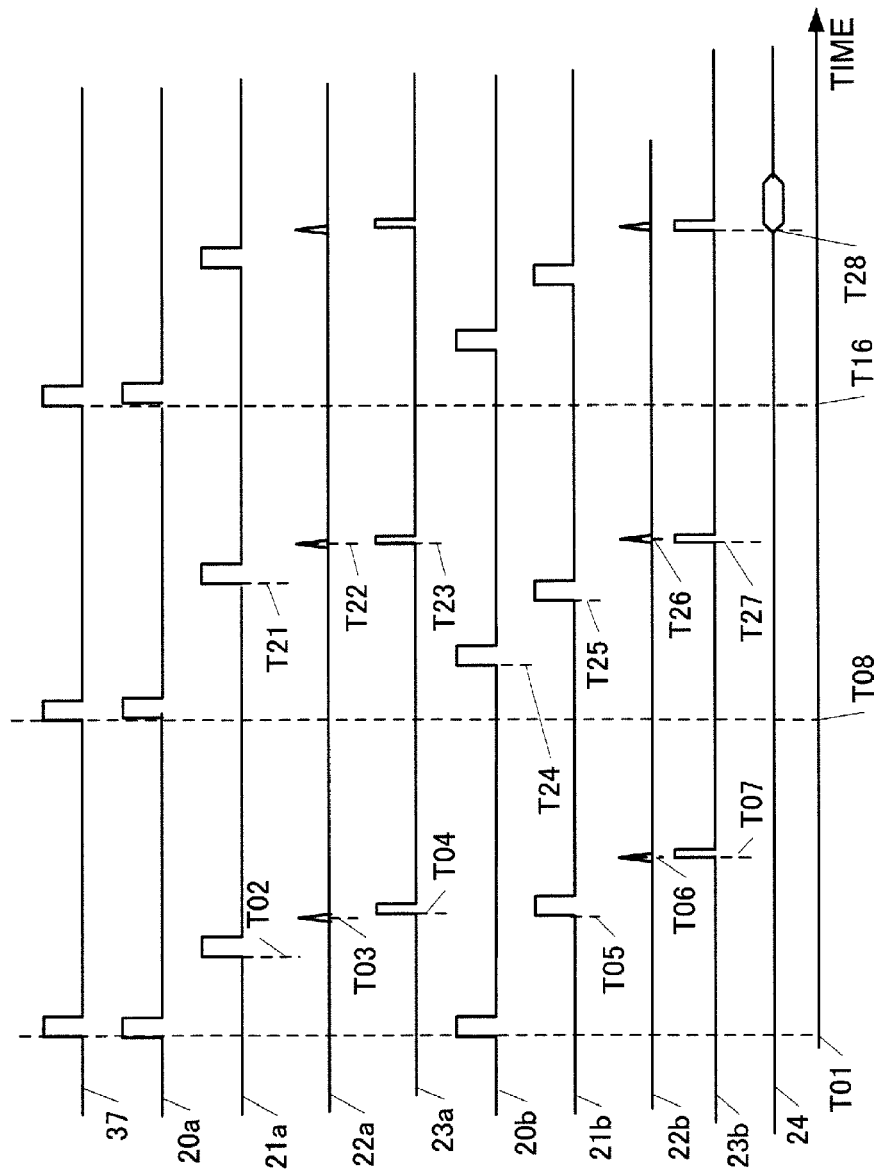
[FIG. 10]

Description on the operation flow in FIG. 2 and the control signal generation circuit 30 in FIG. 3, which is the same as first example, is omitted. A difference of this example from first example is the content of the emission timing adjustment processing in step S5. Details of the emission timing adjustment processing will now be described with reference to a flow chart in FIG. 9 and a timing chart in FIG. 10. Description on step S50 to step S54, which is the same as step S20 to step S24 in first example, is omitted. In the timing chart in FIG. 10, time T01 to time T08 and time T16 are the same as those in FIG. 4.

Then in step S55, the CPU 11 accesses the light quantity measuring circuit 16, reads the values of the light quantity P22a of the pulsed light 22a and the light quantity P22b of the pulsed light 22b, and stores these values in the internal memory.

Description on step S56, which is the same as step S25 in first example, is omitted. If the time difference between the electric pulse signal 23a and the electric pulse signal 23b is within the tolerance, the CPU 11 determines that the timings of the pulsed lights match in step S56, and processing advances to step S57. If the time difference is outside the tolerance, processing advances to step S58.

In Step S57, the CPU 11 compares the light quantity P22a and the light quantity P22b with a tolerance which is set in the CPU 11 in advance, and determines whether these values are within the tolerance. If they are within the tolerance, the CPU 11 ends adjustment of emission timings since both the light quantities and time differences are within the tolerance. If at least one of P22a and P22b is outside the tolerance, processing advances to step S58 and the CPU 11 continues processing.

In step S58, the CPU 11 changes the values in the register 31 so as to decrease the time difference which was read in step S54, and adjusts the quantity of the pulsed lights to be closer to a target value. The target value of the quantity of the pulsed light is determined in advance depending on the intensity of the photoacoustic waves from the plate members 6a and 6b, the frequency characteristics of the probe 5 and the like, and are assumed to be stored in the CPU 11.

If it is determined that the light quantity P22a is greater than the target value, the CPU 11 decreases the value of the oscillation delay setting register R5 for the pulse laser source 2a, and decreases the excitation time so that the energy to be stored in the laser medium is decreased. If it is determined that the light quantity P22a is smaller than the target value, on the other hand, [the CPU 11] increases the value of the oscillation delay setting register R5 for the pulse laser source 2a, and increases the excitation time so that the energy to be stored in the laser medium is increased.

Here the differences of the light quantity P22a and the light quantity P22b from the target value are called a "light quantity error" respectively, and are denoted by P22a_E and P22b_E. The CPU 11 subtracts "K1×P22a_E" from the value of the oscillation delay setting register R5 for the pulse laser source 2a. The CPU 11 also subtracts "K2×P22b_E" from the value of the oscillation delay setting register R6 for the pulsed laser light source 2b. K1 is a positive constant which indicates a control quantity to increase the light quantity of the pulse laser source 2a, and is adjusted in advance and is stored in the CPU 11. K2 is a positive constant which indicates a control quantity to increase the light quantity of the pulse laser source 2b, and is adjusted in advances and is stored in the CPU 11.

For example, if the value of the register R5 is 150000 [ns] and K1×P22a_E=−5000 [ns], the value of the register R5 is changed to 155000. If the value of the register R6 is 152000 [ns] and K2×P22b_E=10000 [ns], the value of the register R6 is changed to 142000.

If the value of P22a_E is positive, the value of "K1× P22a_E" also becomes positive, and the value of the oscillation delay setting register R5 for the pulse laser source 2a becomes smaller than the value which was set in step S51. In other words, by the decrease of the excitation time, it is expected that the energy to be stored in the laser medium decreases, and the quantity of the pulsed light 22a decreases and approaches the target value.

If the value of P22a_E is negative, the value of "K1×P22a_E" also becomes negative, and the value of the oscillation delay setting register R5 for the pulsed laser source 2a becomes greater than the value which was set in step S51. In other words, by the increase of the excitation time, it is expected that the energy to be stored in the laser medium increases, and the quantity of the pulsed light 22a increases and approaches the target value.

This is the same for P22b_E and the oscillation delay setting register R6 for the pulse laser source 2b.

The CPU 11 also writes an absolute value of a total of the value of the time difference "T07−T04" read in step S54 and the value of "K1×P22a_E−K2×P22b_E" in the excitation delay setting register R3.

For example, if T07−T04=2200 [ns], K1×P22a_E=−5000 [ns], and K2×P22b_E=10000 [ns], then 12800 is written in the excitation delay setting register R3. If the total of the value of the time difference "T07−T04" and "K1×P22a_E−K2× P22b_E" is 0 or more, 1 is written in the selection setting register R4. If this value is negative, on the other hand, 0 is written in the selection setting register R4. For example, if T07−T04=2200 [ns], K1×P22a_E=−5000 [ns] and K2×P22b_E=10000 [ns], 0 is written in the selection setting register R4.

Processing then returns to step S51 and the CPU 11 continues processing.

Then the reference pulse signal 37 is output at the time T08, which is 100 milli seconds after the time T01. Since the value of the excitation delay setting register R3 is 12800, a pulse signal is output from the delay circuit 33 at 12.8 micro seconds after the time T08 (at time T24). Since the value of the selection setting register R4 is 0, a pulse signal is output for the excitation start signal 20a at time T08, and a pulse signal is output for the excitation start signal 20b at time T24. In other words, the start of turning ON the flash lamp of the pulse laser source 2b is 12.8 micro seconds delayed from the start of turning ON the flash lamp of the pulse laser source 2a.

The value of the oscillation delay setting register R5 for the pulse laser source 2a is changed from 150000 to 155000 in step S58. Therefore the time difference "T21−T08" between the oscillation start signal 21a and the excitation start signal 20a becomes 155 micro seconds, which is a 5 micro second increase. Due to this, the energy storing time in the laser medium of the pulse laser source 2a becomes longer than the first time, and the quantity of the pulsed light 22a can be increased.

When a pulse signal is output for the oscillation start signal 21a at time T21, the Q switch turns ON in the pulse laser source 2a, and rapid amplification and oscillation of the excitation energy occur. Then the pulsed light 22a is output at several 100 nano seconds later (time T22). After several nano seconds of delay in the optical sensor 4a, the electric pulse signal 23a is output (time T23).

The value of the oscillation delay setting register R6 for the pulse laser source 2b is changed from 152000 to 142000 in step S58. Therefore the time difference "T25−T24" between the oscillation start signal 21b and the excitation start signal 20b becomes 142 micro seconds, that is a 10 micro second decrease from the first time. Due to this, the energy storing time in the laser medium of the pulse laser source 2b becomes shorter than the first time, and the quantity of the pulsed light 22b can be decreased.

When a pulsed signal is output for the oscillation start signal 21b at time T25, the Q switch turns ON in the pulse laser source 2b, and rapid amplification and oscillation of the excitation energy occur. Then the pulsed light 22b is output at several 100 nano seconds later (time T26). After several nano seconds of delay in the optical sensor 4b, the electric pulse signal 23b is output (time T27).

In this example, the time differences "T21−T08" and "T25−T24" between the start of excitation and the start of oscillation are changed, whereby the energy stored in each pulse laser source is increased or decreased, so as to minimize the discrepancy of the quantity of the pulsed light and the target value. By shifting the excitation start timings of a plurality of pulse laser sources based on this change, the discrepancy of the timings of the pulsed lights can be prevented.

If the discrepancy of the emission timings of the electric pulse signals 23a and 23b and the discrepancy of the quantity values of the pulsed lights 22a and 22b become within the tolerance by this timing control, the emission timing adjustment processing ends. Then the pulsed light irradiation onto the subject is started by the processing in step S6 and later (time T16). Here the CPU 11 does not change the register values inside the control circuit 13, hence the pulse laser sources are controlled at the same timings as time T08 to time T16. Reception of the photoacoustic signal is started synchronizing with the electric pulse signal 23a or the electric pulse signal 23b (time T28).

Figure 11A:
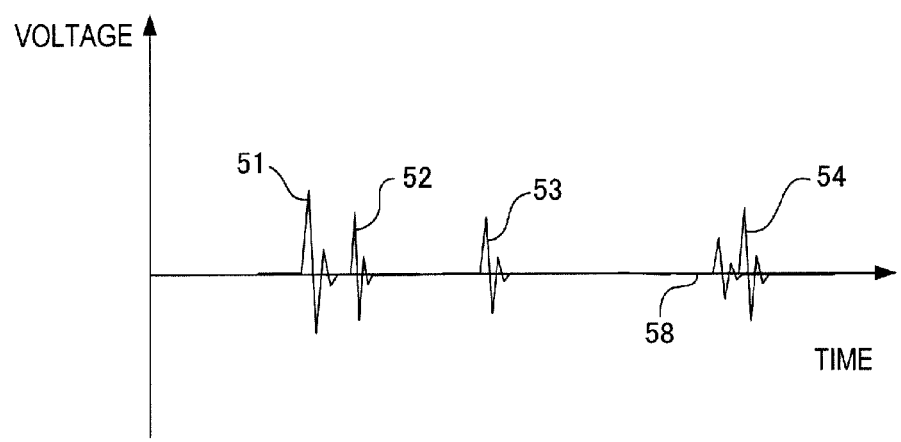
[FIG. 11A]
Figure 11B:
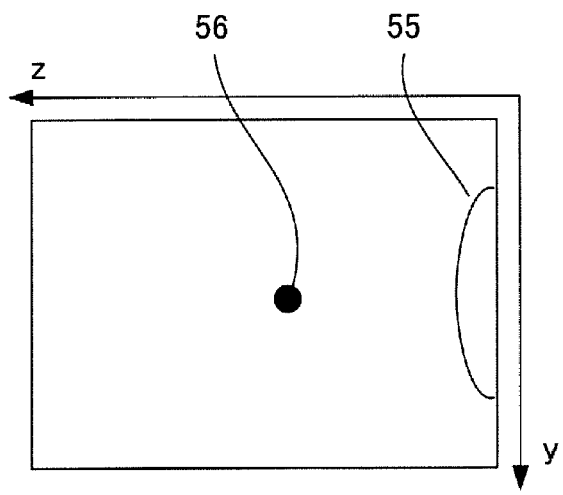
[FIG. 11B]

FIG. 11A and FIG. 11B show an example of a photoacoustic signal waveform and a diagnostic image according to this example. FIG. 11A is an example of the photoacoustic signal which is output from the probe. The abscissa indicates time, and the ordinate indicates voltage. FIG. 11B is a diagnostic image created by converting the photoacoustic signal.

In this example, the pulsed lights 22a and 22b are irradiated onto the subject 1 almost simultaneously at time T28. The interval of the excitation start signal and the oscillation start signal is adjusted so as to decrease the quantity of the pulsed light 22b in step S58. Thereby the photoacoustic waves generated from the surfaces of the plate member 6b and the subject 1 are weakened, and the voltages of the photoacoustic signals 51 and 52 decrease and converge in a short time. As a result, artifact 55 in the corresponding diagnostic image can be decreased.

Furthermore the interval of the excitation start signal and the oscillation start signal is adjusted so as to increase the quantity of the pulsed light 22a in step S58. Thereby the total of the quantity values of the pulsed lights 22a and 22b, which are irradiated to the light absorbing area 7, remains unchanged, and the voltage of the photoacoustic signal 53 is approximately the same as the case of first example. As a result, the contrast of an image 56 in the diagnostic image can be maintained.

On the other hand, due to the increase of the quantity of the pulsed light 22a, the voltage of the photoacoustic signal 54, generated from the surfaces of the plate member 6a and the subject 1, increases more than the case of first example. The influence of the photoacoustic signal 54 on the diagnostic image, however, can be prevented by not using the signals after time 58, when the photoacoustic wave generated from the surfaces of the subject 1 and the plate member 6a propagates, for generating the diagnostic image.

In this example, a case of adjusting the emission timing before measuring the subject was described, but the emission timing may be adjusted during measurement just like second example. Thereby the discrepancies of the quantity of the pulsed light and the timings due to the rise of temperature of the pulse laser sources during measurement, and other causes can be decreased, and an image with less artifacts can be obtained.

For the index to change the excitation time, the integrated values of the electric pulse signals from the optical sensors 4a and 4b, was used in this example, but the present invention is not limited to this method. For example, the photoacoustic signal 51 from the plate member 6b is detected by the signal processing circuit 14, and the value of this voltage is compared with an allowable value stored in the CPU 11. If the voltage of the photoacoustic signal 51 is greater, the excitation time is controlled to be decreased. If this method is used, artifacts can be decreased with certainty by using a photoacoustic signal, which directly influences the diagnostic image, as the index.

As described above, according to third example of the present invention, if a light quantity error is generated in the first emission, the interval of the excitation start signal and the oscillation start signal is controlled to cancel the light quantity error. The values of the excitation start delay register are set so that the interval controlled at this time and the discrepancy of the timings measured for the first time are both cancelled.

Thereby the energy stored between the turning ON the flash lamp of each pulse laser source 2a and 2b and the start of the Q switch can be controlled, and each quantity of pulsed light can be matched with the target value. By changing the oscillation start timing considering the space of the flash lamp and the Q switch, the timings of a plurality of pulsed lights can be matched at high precision. As a result, both artifacts generated by a discrepancy of the light quantity and a discrepancy of the timings can be decreased, and a higher quality diagnostic image can be obtained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-102312, filed on Apr. 27, 2010, which is hereby incorporated by reference herein in its entirety.

The invention claimed is:

1. A measuring apparatus comprising:
a plurality of laser sources for generating pulsed lights;
a control unit for controlling excitation start timing(s) of said laser sources by outputting an excitation start signal to respective ones of said laser sources, and controlling oscillation start timing(s) of said laser sources by outputting an oscillation start signal to ones of said laser sources after a predetermined time has elapsed from the output of the excitation start signal, so as to generate pulsed lights from said laser light sources;
an acoustic wave receiving unit for receiving an acoustic wave generated in a subject by irradiation of the subject with the pulsed lights; and
a signal processing unit for obtaining information of the subject, using a signal which is output from said acoustic wave receiving unit, wherein
said plurality of laser sources include a first laser source and a second laser source of which preparation time from the start of the excitation to the generation of the pulsed light is longer than that of said first laser source, and
said control unit sets timing of outputting the excitation start signal to said first laser source to follow timing of outputting the excitation start signal to said second laser source according to a difference of the preparation time between said first laser source and said second laser source.

2. The measuring apparatus according to claim 1, wherein said control unit sets the timings of outputting the excitation start signal to said first laser source to follow the timing of outputting the excitation start signal to said second laser source so that a difference of between the timings of generation of the pulsed light from said first laser source and the timing of generation of the pulsed light from said second laser source is within a predetermined tolerance.

3. The measuring apparatus according to claim 2, further comprising a detecting unit for detecting a difference of the timings of generation of the pulsed light from said first laser source and the timing of generation of the pulsed light from said second laser source,
wherein said control unit sets the timings of outputting the excitation start signal to said the first laser source to follow the timing of outputting the excitation start signal to said second laser source so that the difference of the timings of generation of the pulsed light detected by said detecting unit is within the tolerance.

4. The measuring apparatus according to claim 3, wherein said signal processing unit does not use a signal that is output from said acoustic wave receiving unit for obtaining information of the subject when the difference of the timings of generation of the pulsed light detected by said detecting unit is outside the tolerance.

5. The measuring apparatus according to claim 3, further comprising a light interrupting unit for interrupting the pulsed lights irradiated from said sources to the subject, while said control unit is adjusting the difference of the timings to output the excitation start signal.

6. The measuring apparatus according to claim 1, wherein said acoustic wave receiving unit performs measurement while moving, and
said control unit determines timing of outputting the excitation start signal to one of said laser sources so that timing when said acoustic wave receiving unit reaches a measuring position and timing of generation of a pulsed light are synchronized.

7. The measuring apparatus according to claim 1, further comprising a light quantity measuring unit for measuring light quantity of pulsed light generated from each of said laser sources,
wherein said control unit changes a length of time between the timing to output the excitation start signal and the timing to output the oscillation start signal so that the light quantity measured by said light quantity measuring unit approaches a predetermined target value.

8. The measuring apparatus according to claim 1, wherein said control unit changes a length of time between the timing of outputting the excitation start signal and the timing of outputting the oscillation start signal so that an intensity of the signal which is output from said acoustic wave receiving unit becomes smaller than a predetermined allowable value.

9. A measuring apparatus comprising:

a plurality of laser sources for generating pulsed lights;

a control unit for controlling excitation start timing(s) of laser sources of said plurality of laser sources by outputting an excitation start signal to respective ones of said laser sources, and controlling an oscillation start timing of the respective ones of said laser sources by outputting an oscillation start signal to the respective ones of said laser sources after a predetermined time has elapsed from the output of the excitation start signal, so as to generate pulsed lights from said laser sources;

an acoustic wave receiving unit for receiving an acoustic wave generated in a subject by irradiation of the subject with the pulsed lights; and a signal processing unit for obtaining information of the subject, using a signal which is output from said acoustic wave receiving unit, wherein said plurality of laser sources include a first laser source and a second laser source, and said control unit makes a timing of outputting the excitation start signal to said first laser source different from a timing of outputting the excitation start signal to said second laser source.

10. The measuring apparatus according to claim 9, further comprising a detecting unit for detecting a difference of the timings of generation of the pulsed light from said first laser source and the timing of generation of the pulsed light from said second laser source, wherein said control unit sets the timings of outputting the excitation start signal to said the first laser source to follow the timing of outputting the excitation start signal to said second laser source so that the difference of the timings of generation of the pulsed light detected by said detecting unit is within the tolerance.

* * * * *